United States Patent [19]
Deguchi et al.

[11] Patent Number: 6,121,381
[45] Date of Patent: Sep. 19, 2000

[54] COMPOSITION CONTAINING URETHANE (METHA)ACRYLATE IN POLYMER

[75] Inventors: Mikito Deguchi, Kyoto; Hiroyuki Shioi, Higasiosaka, both of Japan

[73] Assignee: Kabushiki Kaisha Shofu, Kyoto, Japan

[21] Appl. No.: 09/024,103

[22] Filed: Feb. 17, 1998

[51] Int. Cl.[7] .................................................. C08L 75/16
[52] U.S. Cl. ........................ 525/126; 525/131; 525/278
[58] Field of Search .................................. 525/126, 131, 525/278

[56] References Cited

U.S. PATENT DOCUMENTS

| | | | |
|---|---|---|---|
| 4,223,099 | 9/1980 | von Harpe | 525/126 |
| 4,396,476 | 8/1983 | Roemer | 204/159.16 |
| 5,403,188 | 4/1995 | Oxman | 433/218 |

*Primary Examiner*—Patricia A. Short
*Attorney, Agent, or Firm*—Stevens, Davis, Miller & Mosher, L.L.P.

[57] ABSTRACT

The present invention relates to a curable composition in which polymer and monomer which is neither soluble nor swellable (able to swell) in the polymer are mixed homogeneously. More particularly, the present invention relates to a curable composition, in which polymer and urethane metha(acrylate) which is neither soluble nor swellable in the polymer are mixed homogeneously. The present invention also relates to a cured composition of the curable composition.

19 Claims, 5 Drawing Sheets

COMPOSITION CONTAINING URETHANE (METHA)ACRYLATE IN POLYMER

BACKGROUND OF THE INVENTION

1. Field of the Invention

The present invention relates to a new composition containing modified polymerizable monomer in polymer. More particularly, the present invention relates to a curable composition in which polymer and monomer which is neither soluble nor swellable (able to swell) in the polymer are mixed homogeneously.

The composition of the present invention can be applied to a dental materials and is being used as a artificial teeth material, denture base material, relining material, restorative material, an adhesive material etc. The cured composition may be applied not only to dental materials, but also to general industrial materials, such as adhesives, molding materials and coating compounds etc.

2. Description of the Prior Art

Interpenetrating polymer network (referred to as "IPN" hereinafter) has been known as one of methods to improve dynamic properties of polymer.

IPN is polymer network in which not less than two polymer network chains intertwine complicatedly without covalent binding to improve mechanical strength and physical properties. A basic method of production of IPN is such that polymer, prepolymer and monomer are mixed mechanically with crosslinking agent and catalyst to give a liquid mixture, a solution mixture or a bulk mixture and then the mixture is polymerized to form interpenetrating network structure partially or entirely.

However, the above conventional method is restricted by the mixing method and compatibility of the components. In particular, it is very difficult to mix polymer with monomer non-swellable in the polymer from the viewpoint of molecular level to form IPN.

SUMMARY OF THE INVENTION

The present invention is to provide a curable polymeric composition in which polymer and monomer which is neither soluble nor swellable in the polymer are mixed homogeneously from the viewpoint of molecular level.

The present invention is further to provide a cured composition having both toughness and transparency which are derived from the characteristics of one polymer and the characteristics of the other polymer of the monomer by homogeneously interpenetrating not less than two polymer chains each other in the composition.

The present invention is still further to provide a curable composition and/or cured composition thereof, with fillers, polymerization catalysts, ultraviolet ray-absorbing agents, X-ray impermeable agents etc. added therein, being suitable for applying it to dental restorative materials, more particularly, artificial teeth, denture base materials, relining materials, fillers, adhesive materials, etc., or general industrial materials, such as molding materials, adhesives and coating compounds.

DETAILED DESCRIPTION OF THE INVENTION

Figure 1:
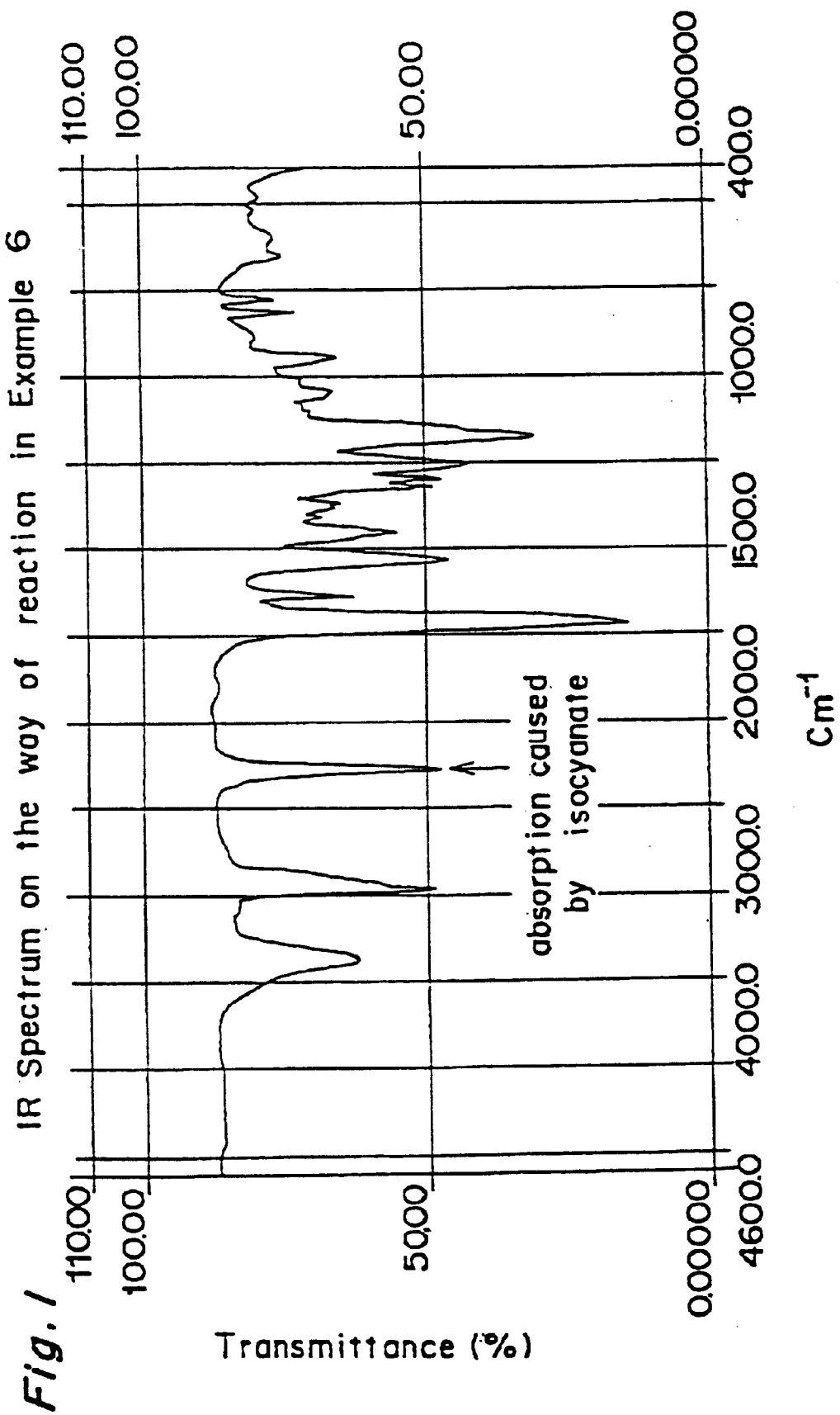
FIG. 1 shows IR chart measured on the way of reaction.

The present invention relates to a curable composition in which polymer and urethane (metha)acrylates which are neither soluble nor swellable in the polymer are mixed homogeneously. The expression "(metha)acrylates" means to include both acrylates and methacrylates. The expression "neither soluble nor swellable in polymer" means that polymer and polymerizable urethane (metha)acrylate monomer swell or dissolve homogeneously to form a transparent mixed solution with high viscosity and that polymer particles are not observed and polymer does not settle with time in the mixed solution. The present invention is characterized by that urethane (metha)acrylates which are neither soluble nor swellable in polymer are mixed homogeneously with the polymer.

Such a composition may be obtained by reacting an isocyanate compound in a homogeneous solution containing polymer with a (metha)acrylate compound having hydroxyl group, or in a reverse order, that is,. by reacting a (metha) acrylate compound having hydroxyl group in a homogeneous solution containing polymer with an isocyanate compound.

Urethane (metha)acrylate is homogeneously mixed with polymer from the viewpoint of molecular level in the resultant composition. Such a composition has high transparency and cured composition thereof shows characteristics, such as increase in crosslink density, fineness of phase organization and increase in inter-phase adhesion etc.

The polymers used in the present invention may be exemplified by poly(alkyl(metha)acrylate), such as poly (methyl methacrylate) (referred to as "PMMA" hereinafter) and poly(ethyl methacrylate) (referred to as "PEMA" hereinafter), copolymer of such alkyl (metha)acrylates, poly (vinyl acetate), copolymer of ethylene with vinyl acetate, polyacrylonitrile, polybutadiene, polystyrene, poly(vinyl chloride), copolymers thereof, and a mixture thereof. These polymers are soluble or swellable in (metha)acrylates having hydroxyl groups, or aliphatic, alicyclic or aromatic isocyanates, such as trimethylhexamethylene diisocyanate (referred to as "TMDI" hereinafter). The polymers are required to be dissolved or swelled homogeneously in (metha)acrylates having hydroxyl groups or isocyanates when mixed so that a transparent mixed solution having high viscosity can be given. From such a viewpoint, it is suitable to use polymers having a mean molecular weight of 100,000 to 1,000,000, preferably 200,000 to 800,000.

The (metha)acrylates having hydroxyl groups used appropriately in the present invention are exemplified by 2-hydroxyethyl methacrylate (referred to as "2-HEMA" ), 3-hydroxypropyl methacrylate, 4-hydroxybutyl methacrylate, 5-hydroxypentyl methacrylate, 6-hydroxyhexyl methacrylate, 2-hydroxy-3-phenyloxypropyl methacrylate (referred to as "2-HFPA"), 2-hydroxyethyl acrylate, 3-hydroxypropyl acrylate etc., preferably 2-HEMA, 2-HFPA, 3-hydroxypropyl methacrylate, more preferably 2-HEMA, 2-HFPA.

Isocyanates appropriately used in the present invention are exemplified by TMDI, hexamethylene diisocyanate (referred to as "HMDI"), bisphenol A diisocyanate, dicyclohexyldimethylmethane diisocyanate, isophorone diisocyanate (referred to as "IPDI"), tolylene diisocyanate, xylylene diisocyanate, diphenylmethane diisocyanate, naphthalene diisocyanate, preferebly TMDI, HMDI, IPDI, more preferably TMDI, HMDI.

Polyisocyanates having isocyanate groups at the end may be used, which are prepared by reacting polyols with excessive diisocyanates. Such polyols are exemplified by ethylene glycol, diethylene glycol, triethylene glycol, tetraethylene glycol, propylene glycol, 1,4-butanediol, 2,3-butanediol, 1,1,1-trimethylolpropane, glycerine. The diisocyanates as above mentioned can be used without any trouble.

The curable composition of the present invention may be obtained as follows. For example, (metha) acrylates having hydroxyl groups, such as 2-HEMA, are put into a flask and nitrogen gas is introduced into the flask. The ingredients are heated to 40–50° C., stirred at 50–80 rpm, and added with the polymers little by little to be completely dissolved or swelled.

Then, tin catalyst used generally for synthesis of urethane is dissolved. The inside of the flask was replaced with oxygen gas. Isocyanate compounds are dropped for 2–3 hours while introducing oxygen gas into the flask. In general, the isocyanates are added a little excessively. After dropping, the ingredients are heated to 70±1° C. to give an object.

In reverse order, after TMDI etc. is put into a flask, 2-HEMA etc. may be added.

When the polyisocyanates having isocyanate groups at the end are used, polyalcohols (the number of hydroxyl group: 2–4) are reacted with isocyanates in a homogeneous solution containing polymers, and then isocyanate groups at the end are reacted with (metha)acrylates having hydroxyl groups.

An addition amount of polymers is approximately 5.2–47 g on the basis of one mole of isocyanate compound used for preparing, for example, (methacryloxyethyl) trimethylhexamethylene diurethane (referred to as "UDMA" hereinafter).

The curable composition of the present invention may further contain polymerizable monomers, if necessary. Such polymerizable monomers may be exemplified by MMA, ethyl (metha)acrylate, butyl (metha)acrylate, hydroxyalkyl ester, such as 3-hydroxypropyl methacrylate and 2-HEMA, perfluorooctyl (metha)acrylate, hexafluorobutyl (metha) acrylate, ethylene glycol di(metha)acrylate (referred to as "EG"), propylene glycol di(metha)acrylate (referred to as "PG"), triethylene glycol di(metha)acrylate (referred to as "TG"), butylene glycol di(metha)acrylate, trimethylolpropane trimethacrylate (referred to as "TMP" hereinafter), 2,2-bis[4-phenyl]propane di(metha)acrylate (referred to as "D-2.6E" hereinafter), urethane di(metha)acrylate, and urethane tri(metha)acrylate, preferably MMA, 2-HEMA, EG, PG, D-2.6E, urethane di(metha)acrylate, and urethane tri (metha)acrylate, more preferably MMA, 2-HEMA, EG, PG, D-2.6E, and urethane di(metha)acrylate.

These polymerizable monomers may be contained singly or in combination depending on a desired use at an amount of 70–2 parts by weight on the basis of 30–98 parts by weight of the curable composition.

Inorganic fillers or organic fillers may be contained to improve wear resistance while toughness is kept. An adequate fill of the fillers is 40–75 parts by weight (including the polymerizable monomers when those polymerizable monomers are made contained) on the basis of 25–60 parts by weight of the curable composition. Examples of adequate inorganic fillers are silica and alumina having a mean particle size of about 3 nm–100 nm and treated with silanes. Examples of adequate organic fillers are the one having a mean particle size of about 5–20 μm in which DMA-ethylene glycol dimethacrylate and dry silica (highly dispersal silicon dioxide) are mixed and polymerized to be pulverized. The organic fillers and the inorganic fillers may be used singly or in combination.

The composition of the present invention may be dissolved at an amount of 0.1 to 10 parts by weight in 90 to 99.9 parts by weight of a solvent, such as methylene chloride, acetone, methyl ethyl ketone, ethyl acetate, butyl acetate.

The composition of the present invention is preferably polymerized at a temperature of 50 to 150° C . Peroxide catalyst is added at an amount of 0.1 to 3 parts by weight on the basis of 100 parts by weight of a total amount of polymerizable compounds (urethane (metha)acrylate and polymerizable compounds). When polymerization is carried out by ultraviolet rays or visible rays, promoptors or photosensitizers are contained at an amount of 0.2–3 parts by weight on the basis of 100 parts by weight of the composition. Polymerization may be made at ordinary temperature by use of catalyst, such as general peroxides-tertiary amine series. In this case, an addition amount of the catalyst and promoters are adequately 0.3–3 parts by weight. In addition to the above conditions, a pressure of 50–400 Kgf/cm$^2$ may be applied to reaction system.

The curable composition or cured composition of the present invention is excellent in strength, toughness and durability as polymers and urethane (metha)acrylates are interwined from the viewpoint of molecule level to bring about increase in crosslink density, fineness of phase organization and increase in inter-phase adhesion etc. Therefore, the compositions of the present invention are useful as materials excellent in transparency, durability and impact resistance when applied to industrial materials for synthetic resin and dental materials, such as molding materials for resin products, materials for artificial teeth, and composite materials.

In more detail, dental resins are conventionally used by generally mixing PMMA with methyl methacrylate (referred to as "MMA" hereinafter). When a part or all of MMA is replaced by the compositions of the present invention, strength and impact resistance can be improved. When the inorganic fillers are further mixed, toughness required of dental composite resins, adhesion strength and fatigue resistance required of adhesives for dentins and plate resin can be improved by leaps and bounds.

Moreover, when monofunctional or polyfunctional monomers, polymerizable monomers containing acidic groups, photosensitizers and accelerators etc. are mixed, the composition can be applied to photopolymerizable adhesives for dentins and restorative dental materials.

The solubility and swellability referred to in the present invention is explained in more detail by Examples 1–2 and Comparative Examples 1–4.

EXAMPLE 1

2-HEMA (250 ml) was added with PEMA of 0, 1, 3, 5, 7, 10, 15 and 20 g respectively and stirred at 50±1° C. for 24 hours. Sample of 250 g was put in a brown glass vessel and left to stand at 23±1° C. for 24 hours in a thermostatic chamber. Then, viscosity was measured by means of B-model viscometer (BL model No. 3 rotor) after 5 minutes. Transmittance was measured in the wavelength range between 780 nm and 380 nm by means of spectrophotometer U-3200 (made by Hitachi Seisakusyo K.K.)

EXAMPLE 2

Example 2 was carried out in a manner similar to Example 1 except that PMMA was used.

COMPARATIVE EXAMPLE 1

Comparative Example 1 was carried out in a manner similar to Example 1 except that ethylene glycol was used instead of 2-HEMA.

COMPARATIVE EXAMPLE 2

Comparative Example 2 was carried out in a manner similar to Example 1 except that ethylene glycol instead of 2-HEMA and PMMA instead of PEMA were used.

COMPARATIVE EXAMPLE 3

Comparative Example 3 was carried out in a manner similar to Example 1 except that propylene glycol was used instead of 2-HEMA.

COMPARATIVE EXAMPLE 4

Comparative Example 4 was carried out in a manner similar to Example 1 except that propylene glycol instead of 2-HEMA and PMMA instead of PEMA were used.

Viscosity and transmittance obtained in Examples 1–2 and Comparative Examples 1–4 are shown in Table 1 and Table 2. The solubility or swellability of hydroxyl group-containing compounds to the polymer can be read in Table 1 and Table 2. When solubility or swellability is high, transmittance does not decrease with addition of polymer and viscosity becomes very high because of homogeneity of monomer and polymer. Mere dispersion without such solubility or swellability has constant viscosity, and transmittance becomes remarkably low.

TABLE 1

| Polymer PEMA Addition | Viscosity (CPS) 2-HEMA Example 1 | Viscosity (CPS) EG Comp. Ex. 1 | Viscosity (CPS) PG Comp. Ex. 3 | Transmittance (%) Example 1 | Transmittance (%) Comp. Ex. 1 | Transmittance (%) Comp. Ex. 3 |
|---|---|---|---|---|---|---|
| 0 pbw | 13 | 25 | 49 | 100.8 | 100.6 | 100.4 |
| 1 pbw | 16 | 25 | 50 | 100.9 | 27.1 | 47.7 |
| 3 pbw | 40 | 25.5 | 51.5 | 100.8 | 7.2 | 20.5 |
| 5 pbw | 80.5 | 25.5 | 52.5 | 100.6 | 3.8 | 10.3 |
| 7 pbw | 202 | 28 | 57 | 100.1 | 2.6 | 8.4 |
| 10 pbw | 605 | 28 | 66 | 99.9 | 1.9 | 5.2 |
| 15 pbw | 4800 | 37.5 | 83.5 | 99.4 | 1.4 | 3.1 |
| 20 pbw | 25250 | 45 | 90 | 98.9 | 1.1 | 2.6 |

TABLE 2

| Polymer PMMA Addition | Viscosity (CPS) 2-HEMA Example 2 | Viscosity (CPS) EG Comp. Ex. 2 | Viscosity (CPS) PG Comp. Ex. 4 | Transmittance (%) Example 2 | Transmittance (%) Comp. Ex. 2 | Transmittance (%) Comp. Ex. 4 |
|---|---|---|---|---|---|---|
| 0 pbw | 11.5 | 21.5 | 49.5 | 100.6 | 100.0 | 100.4 |
| 1 pbw | 27 | 22 | 49.5 | 100.8 | 64.6 | 68.5 |
| 3 pbw | 231 | 22.5 | 50.5 | 100.5 | 35.1 | 37.1 |
| 5 pbw | 2015 | 23.5 | 53 | 101.7 | 21.2 | 24.9 |
| 7 pbw | 12490 | 24 | 57 | 100.7 | 13.8 | 14.6 |
| 10 pbw | 32600 | 26 | 59.5 | 101.3 | 8.9 | 10.8 |
| 15 pbw | Rubber-like | 27.5 | 63 | 100.3 | 5.9 | 7.3 |
| 20 pbw | Rubber-like | 32.5 | 69 | 100.4 | 5.0 | 5.4 |

EXAMPLE 3

(synthesis of curable composition of the present invention)

2-HEMA of 260.3 g (2 mole) was put in a glass flask with agitating blade. The content was heated to 40–50° C. while nitrogen gas was introduced into the flask. PMMA of 5.2 g was added little by little for 3–5 hours while the contents were stirred at 50–80 rpm, so that PMMA was completely swelled and dissolved.

The obtained solution was added with 110 mg of dibutyltin dilaurate. After addition, the introduction of nitrogen gas was stopped. The inside of the flask was replaced with oxygen gas. While oxygen gas was introduced, 210.3 g (1 mole) of TMDI was added dropwise for 2 hours. After dropping, the contents were heated to 70±1° C. Addition reaction was continued until all isocyanate groups were reacted to give UDMA. End point of the reaction was confirmed by isocyanate-equivalence titration method. Yield was 98.6%.

The confirmation of endpoint of the reaction by isocyanate-equivalence titration method was made as follows;

① Sample of 3 g is precisely weighed and put in a conical flask with a stopper.

② Di-n-butylamine solution of 50 ml is added to the flask and left to stand for 15 minutes.

③ After isopropyl alcohol (first grade) of 20 ml is added, three to four droplets of bromocresol green indication (bromocresol green of 0.1 g is added with 1.5 ml of N/10 sodium hydroxide solution, ground and dissolved, and then water is added, so that total volume can be 100 ml) are added. The contents are shook and mixed sufficiently. The resultant solution is titrated with N/2 hydrochloric acid. At near endpoint of the reaction, N/2 hydrochloric acid solution is added droplet by droplet. After every addition of the droplet, the solution is shook. The point when blue or violet-blue disappeared and yellow lasted for at least 15 seconds is recognized to be endpoint of the reaction. Authentic sample is titrated separately under the same conditions. Equivalence of isocyanat=

$$\frac{(B-A) \times f}{2 \times S}$$

in which A is usage (ml) of N/2 hydrochloric acid standard solution to titrate sample; B is usage (ml) of N/2 hydrochloric acid standard solution to titrate authentic sample; f is factor of N/2 hydrochloric acid standard solution; and S is weighed amount (g) of sample.

EXAMPLE 4

A curable composition was synthesized in a manner similar to Example 3, except that 9.4 g of PMMA was used. Yield: 99.5%.

EXAMPLE 5

A curable composition was synthesized in a manner similar to Example 3, except that 5.2 g of PEMA was used as polymer. Yield: 99%.

EXAMPLE 6

A curable composition was synthesized in a manner similar to Example 3, except that 9.4 g of PEMA was used as polymer. Yield: 98%.

Figure 2:
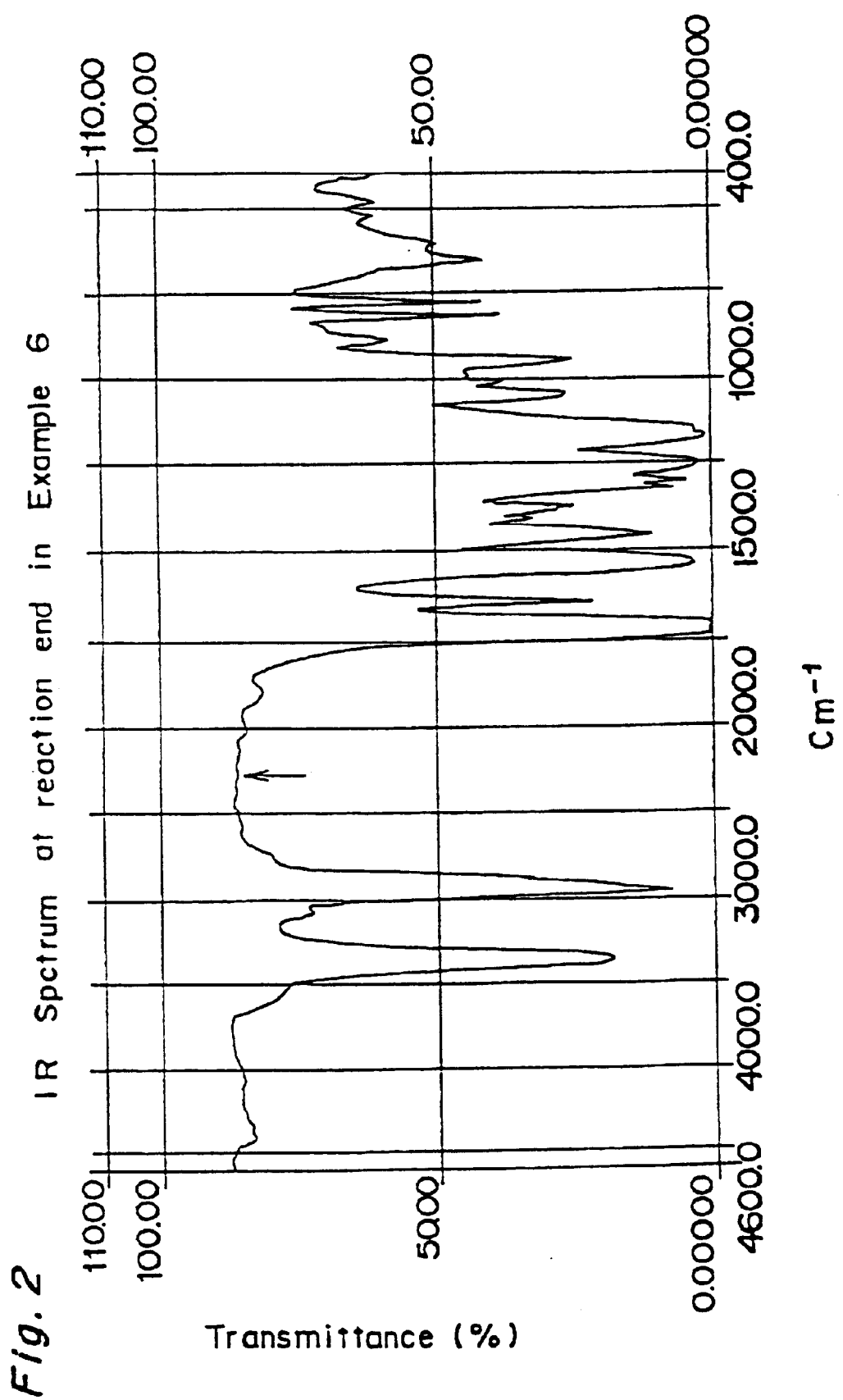
FIG. 2 shows IR chart measured at the end of reaction.

IR spectrum was taken on the way of reaction and at the endpoint of the reaction during measurement by isocyanate equivalence titration method in Example 6. The IR spectra were shown in FIG. 1 and FIG. 2. FIG. 1 was IR spectrum taken on the way of reaction. FIG. 2 was IR spectrum taken at the endpoint of reaction. The absorption caused by isocyanete group dissapears at the endpoint of reaction. Thus, the endpoint of reaction can be confirmed by IR.

EXAMPLE 7

TMDI of 210.3 g (1 mole) was put in a glass flask with agitating blade. The content was heated to 40–50° C. while nitrogen gas was introduced into the flask PEMA of 9.4 g was added little by little for 3–5 hours while the contents were stirred at 50–80 rpm, so that PEMA was completely swelled and dissolved.

The obtained solution was added with 110 mg of dibutyltin dilaurate. After addition, the introduction of nitrogen gas was stopped. The inside of the flask was replaced with oxygen gas. While oxygen gas was introduced, 260.3 g (2 mole) of 2-HEMA was added dropwise for 2 hours. After dropping, the contents were heated to 70±1° C. Addition reaction was continued until all isocyanate groups were reacted. End point of the reaction was confirmed by FT-IR and isocyanate-equivalence titration method. Yield was 98.6%.

EXAMPLE 8

A curable composition was synthesized in a manner similar to Example 7, except that 47 g of PEMA was used. Yield: 98%.

EXAMPLE 9

HMDI of 168.02 g (1 mole) was put in a glass flask with agitating blade. The content was heated to 40–50° C. while nitrogen gas was introduced into the flask. PEMA of 10 g was added little by little for 3–5 hours while the contents were stirred at 50–80 rpm, so that PEMA was completely swelled.

The obtained solution was added with 110 mg of dibutyltin dilaurate. After addition, the introduction of nitrogen gas was stopped. The inside of the flask was replaced with oxygen gas. While oxygen gas was introduced, 444.5 g (2 mole) of 2-HFPA was added dropwise for 2 hours. After dropping, the contents were heated to 50±1° C. Addition reaction was continued until all isocyanate groups were reacted to give 1,6-bis[(2-phenoxy-2'-acryloxy)isopropyloxy-carbonylamino]hexane (referred to as "UDA" hereinafter). End point of the reaction as confirmed by FT-IR and isocyanate-equivalence titration method.

EXAMPLE 10

HMDI of 504.6 g (3 mole) was put in a glass flask with agitating blade. The content was heated to 40–50° C. while nitrogen gas was introduced into the flask. PEMA of 9 g was added little by little for 3–5 hours while the contents were stirred at 50–80 rpm, so that PEMA was completely swelled.

The obtained solution was added with 10 mg of dibutyltin dilaurate. After addition, the introduction of nitrogen gas was stopped. The inside of the flask was replaced with oxygen gas. While oxygen gas was introduced, 134.18 g (1 mole) of trimethylolpropane (referred to as "TMP" hereinafter) was added dropwise for 2 hours. After dropping, the contents were heated to 50±1° C. Addition reaction of one of isocyanate groups of HMDI with TMP was carried out.

After addition reaction, 110 mg of dibutyltin dilaurate was added. After addition, 666.75 g (3 mole) of 2-HFPA was added dropwise for 2 hours. Then, the contents were heated to 70±1° C. Addition reaction was continued until all isocyanate groups were reacted to give three functional urethane acrylate oligomer, 1,1,1-tri[6[(1-acryloxy-3-phenoxy)isopropyloxycarbonylamino]-hexylcarbamoyloxymethyl]propane (referred to as "URO" hereinafter). End point of the reaction was confirmed by FT-IR and isocyanate-equivalence titration method. Yield: 98.5%.

The resultant curable compositions of Examples 3–10 were subjected to FT-IR (FT-300, made by Horiba Seisakusyo K.K.) to measure IR absorption. Average molecular weight and retention time of polymer, and molecular weight and retention time of urethane monomer were measured by means of GPC. Thus, it was confirmed that the obtained compositions were respectively aimed composition. The results are shown in Table 3 and Table 4. In addition, retention time of UDMA, UDA, URO and retention time and molecular weight of PEMA, PMMA, measured by GPC are shown.

TABLE 3

| | IR (Characteristic Absorption of Infrared Rays/cm$^{-1}$) | | | | |
|---|---|---|---|---|---|
| | NH Stretching | CH Stretching | —NHCOO— C=O Stretching | C=C Stretching | CH Deformation |
| Ex. 3 | 3369.03 (m) 3353.60 (m) | 2958.27 (s) 2931.27 (sh) | 1720.29 (vs) | 1637.27 (m) | 1456.06 (m) 1369.21 (w) |
| Ex. 4 | 3370.96 (m) 3351.86 (m) | 2958.27 (s) 2931.27 (sh) | 1720.29 (vs) | 1637.27 (m) | 1456.06 (m) 1369.21 (w) |
| Ex. 5 | 3370.96 (m) 3351.68 (m) | 2958.27 (s) 2931.27 (sh) | 1720.29 (vs) | 1637.27 (m) | 1456.06 (m) 1369.21 (w) |
| Ex. 6 | 3370.96 (m) 3351.86 (m) | 2958.27 (s) 2931.27 (sh) | 1720.29 (vs) | 1637.27 (m) | 1456.06 (m) 1369.21 (w) |
| Ex. 7 | 3369.03 (m) 3353.60 (m) | 2958.27 (s) 2931.27 (sh) | 1720.29 (vs) | 1637.27 (m) | 1456.06 (m) 1369.21 (w) |
| Ex. 8 | 3372.80 (m) 3355.53 (m) | 2958.27 (s) 2931.27 (sh) | 1720.29 (vs) | 1637.27 (m) | 1456.06 (m) 1371.14 (w) |
| Ex. 9 | 3359.39 (m) 3342.03 (m) | 2935.13 (s) 2861.84 (sh) | 1722.12 (vs) | 1635.34 (m) | 1498.42 (m) 1407.78 (w) |
| Ex. 10 | 3365.17 (m) 3353.60 (m) | 2935.13 (s) 2861.84 (sh) | 1725.98 (vs) | 1633.41 (m) | 1496.49 (m) 1407.78 (w) |

The letters VS (Very Strong), S (Strong), m (medium), W (Week) and sh (shoulder) inside the ( ) means absorption strength.

TABLE 4

Results of GPC measurement of Composition

| | Properties of Polymer | | | Properties of Urethane | |
|---|---|---|---|---|---|
| | Species | Molecular weight | Retention time | Species | Retention time |
| Ex. 3 | PMMA | 538256 | 24.27 min. | UDMA | 41.25 min. |
| Ex. 4 | PMMA | 54885 | 24.45 min. | UDMA | 41.50 min. |
| Ex. 5 | PEMA | 401721 | 24.45 min. | UDMA | 41.25 min. |
| Ex. 6 | PEMA | 444607 | 27.77 min. | UDMA | 41.25 min. |
| Ex. 7 | PEMA | 444831 | 24.77 min. | UDMA | 41.25 min. |
| Ex. 8 | PEMA | 464859 | 24.77 min. | UDMA | 41.25 min. |
| Ex. 9 | PEMA | 475869 | 24.64 min. | UDA | 35.45 min. |
| Ex. 10 | PEMA | 485695 | 24.68 min. | URO- | 26.45 min. |
| PMMA | PMMA | 524425 | 24.48 min. | — | — |
| PEMA | PEMA | 459768 | 24.73 min. | — | — |
| UDMA | — | — | — | UDMA | 41.35 min. |
| UDA | — | — | — | UDA | 35.75 min. |
| URO | — | — | — | URO | 26.75 min. |

COMPARATIVE EXAMPLE 5

(Mere mixing in Comparative Examples 5 to 14)

(Comparison with Example 3)

PMMA of 5.2 g was added to UDMA of 1 mole and mixed homogeneously. The mixture was degassed and preserved at 50° C. for 24 hours. Hazen color number and viscosity were measured.

COMPARATIVE EXAMPLE 6

(Comparison with Example 4)

PMMA of 9.4 g was added to UDMA of 1 mole and mixed homogeneously. The mixture was degassed and preserved at 50° C. for 24 hours.

COMPARATIVE EXAMPLE 7

(Comparison with Example 5)

PEMA of 5.2 g was added to UDMA of 1 mole and mixed homogeneously. The mixture was degassed and preserved at 50° C. for 24 hours.

COMPARATIVE EXAMPLE 8

(Comparison with Examples 6 and 7)

PEMA of 9.4 g was added to UDMA of 1 mole and mixed homogeneously. The mixture was degassed and preserved at 50° C. for 24 hours.

COMPARATIVE EXAMPLE 9

(Comparison with Example 8)

PEMA of 47 g was added to UDMA of 1 mole and mixed homogeneously. The mixture was degassed and preserved at 50° C. for 24 hours.

COMPARATIVE EXAMPLE 10

(Comparison with Example 9)

PEMA of 10 g was added to UDA of 1 mole and mixed homogeneously. The mixture was degassed and preserved at 50° C. for 24 hours.

COMPARATIVE EXAMPLE 11

(Comparison with Example 10)

PEMA of 9 g was added to URO of 1 mole and mixed homogeneously. The mixture was degassed and preserved at 50° C. for 24 hours.

COMPARATIVE EXAMPLE 12

Only UDMA was used (UDMA100%).

COMPARATIVE EXAMPLE 13

Only UDA was used (UDA100%).

COMPARATIVE EXAMPLE 14

Only URO was used (URO100%).

The curable compositions obtained in Examples 3–10 and Comparative Examples 5–14 were subjected to measurement on transparency, existence of polymer particles, Hazen color number and viscosity. The results are shown in Table 5.

Transparency was observed visually. When the solution is homogeneous and clear, the composition was judged to be "transparent". The existence of polymer particles was observed visually by applying ray of light to compositions in a specified direction. Judgement of existence of polymer particles was made on the basis of the fact that when particles exist, the composition is suspended at the time of application of ray of light, when particles do not exist, the composition is not suspended.

The Hazen color number was measured according to APHA method of JIS-K6901 (referred to as "APHA" hereinafter).

The measurement of viscosity of compositions in Examples 3–8 and Comparative Examples 5–9 was made as follows. Sample of 250 g was put in a brown glass vessel and left to stand for 24 hours in a thermostatic chamber thermostated at 23±1° C. Then, the sample was subjected to B-type viscometer (BL model No.3 rotor). The measurement was made after 5 minutes.

The measurement of viscosity of compositions in Examples 9 and 10 and Comparative Examples 13 and 14 was made as follows. Sample of 250 g was put in a brown glass vessel and left to stand for 24 hours in a thermostatic chamber thermostated at 50±1° C. Then, the sample was subjected to B-type viscometer (BL model No.3 rotor). The measurement was made after 5 minutes.

The measurement of transmittance (%) of compositions in Examples 3–10 and Comparative Examples 5–14 was made in the range between 780 nm and 380 nm by means of spectrophotometer U-3200 (made Hitachi Seisakusyo K.K.). The size of sample (diameter: 40 mm, thickness: 3 mm).

Then, the compositions of Examples 3–10 and Comparative Examples 5–14 were respectively added with benzoyl peroxide (referred to as "BPO" hereinafter) at content of 0.5% by weight. After dissolution, the composition was polymerized in metal mold under pressure of 100–300 Kgf/cm$^2$ at 80° C. for 5 minutes, and cooled for 5 minutes. Polymerization was further carried out at 120° C. for 10 minutes. After polymerization, annealing was made at 100° C. for 8 hours.

Transmittance and existence of polymer particles were observed with respect to the obtained cured compositions. The results are shown in Table 5.

The existence of polymer particles in the cured compositions was observed under a microscope with a magnification of 100–150. In table 5, "none" means that there existed no interface between matrix and polymer particles in the cured composition and that the composition was homogeneous and transparent. "Observed" means that there existed interface between matrix and polymer particles in the cured composition and that polymer particles existed in spherical form.

TABLE 5

| | Properties of curable composition | | | | Properties of cured composition | |
|---|---|---|---|---|---|---|
| | Transparency | Observation of polymer particles | Hazen color number APHA | Viscosity (CPS) | Transmittance (%) | Observation of polymer particles |
| (EX 3) EX 3 | Transparent | None | 50 | 29500 | 89.0 | None |
| EX 4 | Transparent | None | 40 | 96500 | 88.5 | None |
| EX 5 | Transparent | None | 40 | 18500 | 89.3 | None |
| EX 6 | Transparent | None | 50 | 28500 | 86.0 | None |
| (EX 7) EX 7 | Transparent | None | 50 | 29100 | 86.0 | None |
| EX 8 | Transparent | None | 50 | Unable to measure (rubber-like) | 80.0 | None |
| (EX 9) EX 9 | Transparent | None | 35 | Unable to measure (rubber-like) | 86.4 | None |
| (EX 10) EX 10 | Transparent | None | 40 | Unable to measure (rubber-like) | 88.1 | None |
| Comp. EX 5 | Transparent | Observed | 30 | 9600 | 84.0 | Observed |
| Comp. EX 6 | Transparent | Observed | 30 | 9100 | 83.5 | Observed |
| Comp. EX 7 | Transparent | Observed | 30 | 8400 | 84.8 | Observed |
| Comp. EX 8 | Transparent | Observed | 30 | 9000 | 83.6 | Observed |
| Comp. EX 9 | Transparent | Observed | 30 | 13500 | 66.9 | Observed |
| Comp. EX 10 | Transparent | Observed | 30 | 3350 | 76.7 | Observed |
| Comp. EX 11 | Transparent | Observed | 30 | 3300 | 85.8 | Observed |
| Comp. EX 12 | Transparent | No addition | 20 | 9200 | 90.0 | No addition |
| Comp. EX 13 | Transparent | No addition | 25 | 3350 | 88.5 | No addition |
| Comp. EX 14 | Transparent | No addition | 25 | 3300 | 89.0 | No addition |

EX 3  2-HEMA 260.3 g (2 mole)
 ←PMMA 5.2 g
 ←cat
 ←TMDI 210.3 g (1 mole)
Reaction end (FT-IR, GPC, isocyanate-equivalence titration method)

EX 7  TMDI 210.3 g (1 mole)
 ←PEMA 9.4 g
 ←cat
 ←2-HEMA 260.3 g (2 mole)
Reaction end EX 9  HMDI 168.20 g (1 mole)
 ←PEMA 10 g
 ←cat
 ←2-HFPA 444.5 g (2 mole)
 ←UDA
Reaction end EX 10  HMDI 504.6 g (3 mole)
 ←PEMA
 ←cat
 ←TMP 134.18 g (1 mole)
Addition reaction
 ←cat
 ←2-HFPA 666.75 g (3 mole)
 ←URO
Reaction end It can be understood from Table 5 that the compositions of Examples 3–10 had high transparency compared with the ones of Comparative Examples 5–11, and polymer particles were not observed. The viscosity of the compositions was very high. Polymer particles were not observed in the cured compositions.

As to the cured compositions, specific heat capacity (J/(d.deg)) was also measured. The specific heat capacity was measred by means of DSC 220C made by Seiko Densi Kogyo K.K.). The measurement of specific heat capacity was made according to the following formula:

$$Cps = \frac{Y_s}{Y_r} \times \frac{M_r}{M_s} \times Cpr$$

in which Cps is specific heat capacity of sample;

Cpr is specific heat capacity of standard substance;

Ys is difference of DSC curve between empty vessel and sample;

Yr is difference of DSC curve between empty vessel and standard substance;

Mr is standard substance;

Ms is weight of sample.

Figure 3:
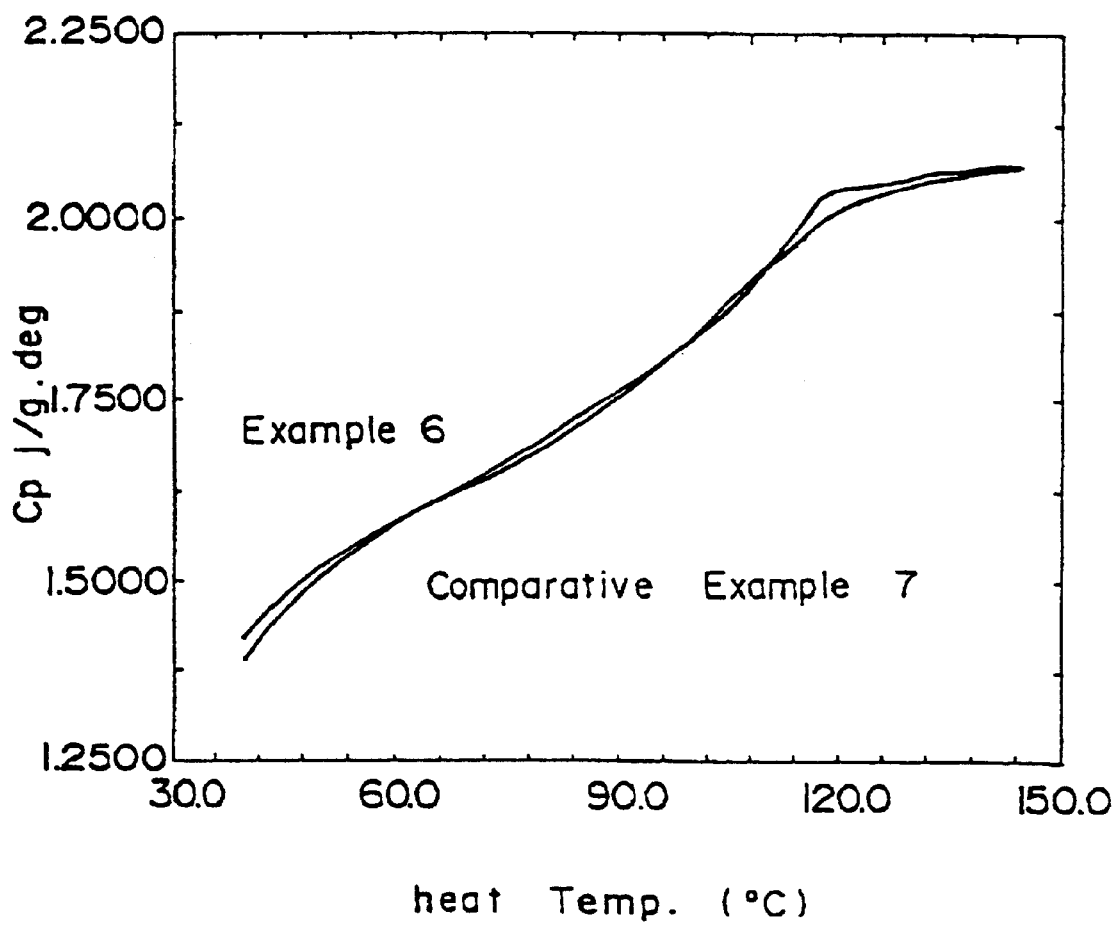
FIG. 3 shows specific heat vs. temperature curve.

The results of specific heat between 40° C. and 140° C. of PEMA and the cured compositions of Examples 5 and 7–10 and Comparative Examples 7–14 are shown in Table 6. Examples of specific heat curves are shown in FIG. 3 with respect to Example 5 and Comparative Example 7, in FIG. 4 with respect to Example 7 and Comparative Example 8, and in FIG. 5 with respect to Example 8 and Comparative Example 9.

position. Then, the monomer composition was mixed with polymer PMMA-2 (average molecular weight: 1,000,000, mean particle size: 8 miron PMMA) at ratio of 2:1 (polymer:monomer composition).

After swelling, the mixture was polymerized in metal mold under pressure of 100–300 Kgf/cm$^2$ at 120° C. for 10 minutes. After polymerization, annealing was made at 100° C. for 8 hours. The obtained cured compositions were subjected to measurement on hardness, bending properties (strength, energy, failing energy) and transmittance. The results are shown in Table 7.

Measurement of hardness was made by use of Hardness Tester DMH-2 (made by Sawamatsu Seiki K.K.) Knoop hardness was measured after sample was preserved in water at 50° C. for 24 hours. Loading was 25 g.

Bending strength was measured by use of Autograph AG 500B (made by Shimazu Seisakusyo K.K.). Samples having size of width (10 mm), thickness (2.5 mm) and length (60 mm) were prepared. The samples were preserved in water at 50° C. for 24 hours, and strength (maximal bending

TABLE 6

Specific Gravity

| | Specific heat capacity (J/g deg) & Measuring temparature (°C.) | | | | | | | | | | |
|---|---|---|---|---|---|---|---|---|---|---|---|
| | 40 | 50 | 60 | 70 | 80 | 90 | 100 | 110 | 120 | 130 | 140 |
| EX 5 | 1.451 | 1.561 | 1.655 | 1.693 | 1.738 | 1.810 | 1.881 | 1.950 | 2.045 | 2.087 | 2.096 |
| EX 7 | 1.461 | 1.555 | 1.635 | 1.684 | 1.743 | 1.810 | 1.897 | 1.998 | 2.077 | 2.123 | 2.154 |
| EX 8 | 1.464 | 1.584 | 1.684 | 1.775 | 1.828 | 1.881 | 1.957 | 2.047 | 2.136 | 2.189 | 2.226 |
| EX 9 | 1.468 | 1.589 | 1.748 | 1.919 | 2.000 | 2.016 | 2.048 | 2.076 | 2.098 | 2.123 | 2.140 |
| EX 10 | 1.497 | 1.627 | 1.795 | 1.904 | 2.043 | 2.105 | 2.133 | 2.148 | 2.172 | 2.188 | 2.195 |
| Comp. EX 7 | 1.419 | 1.518 | 1.579 | 1.635 | 1.693 | 1.762 | 1.839 | 1.934 | 20.41 | 2.056 | 2.075 |
| Comp. EX 8 | 1.415 | 1.511 | 1.572 | 1.629 | 1.686 | 1.747 | 1.811 | 1.891 | 2.000 | 2.023 | 2.051 |
| Comp. EX 9 | 1.319 | 1.458 | 1.539 | 1.639 | 1.683 | 1.727 | 1.789 | 1.859 | 1.943 | 2.001 | 2.045 |
| Comp. EX 10 | 1.428 | 1.551 | 1.718 | 1.906 | 1.971 | 1.988 | 2.021 | 2.045 | 2.067 | 2.086 | 2.106 |
| Comp. EX 11 | 1.423 | 1.575 | 1.753 | 1.895 | 2.028 | 2.055 | 2.070 | 2.031 | 2.085 | 2.091 | 2.092 |
| Comp. EX 12 | 1.387 | 1.503 | 1.578 | 1.632 | 1.684 | 1.757 | 1.842 | 1.935 | 2.012 | 2.044 | 2.066 |
| Comp. EX 13 | 1.393 | 1.536 | 1.744 | 1.919 | 1.934 | 1.956 | 1.980 | 2.007 | 2.025 | 2.044 | 2.061 |
| Comp. EX 14 | 1.389 | 1.525 | 1.673 | 1.771 | 1.898 | 1.965 | 2.003 | 2.08 | 2.037 | 2.052 | 2.057 |
| PEMA | 1.378 | 1.467 | 1.536 | 1.735 | | | | | | | |

Figure 4:
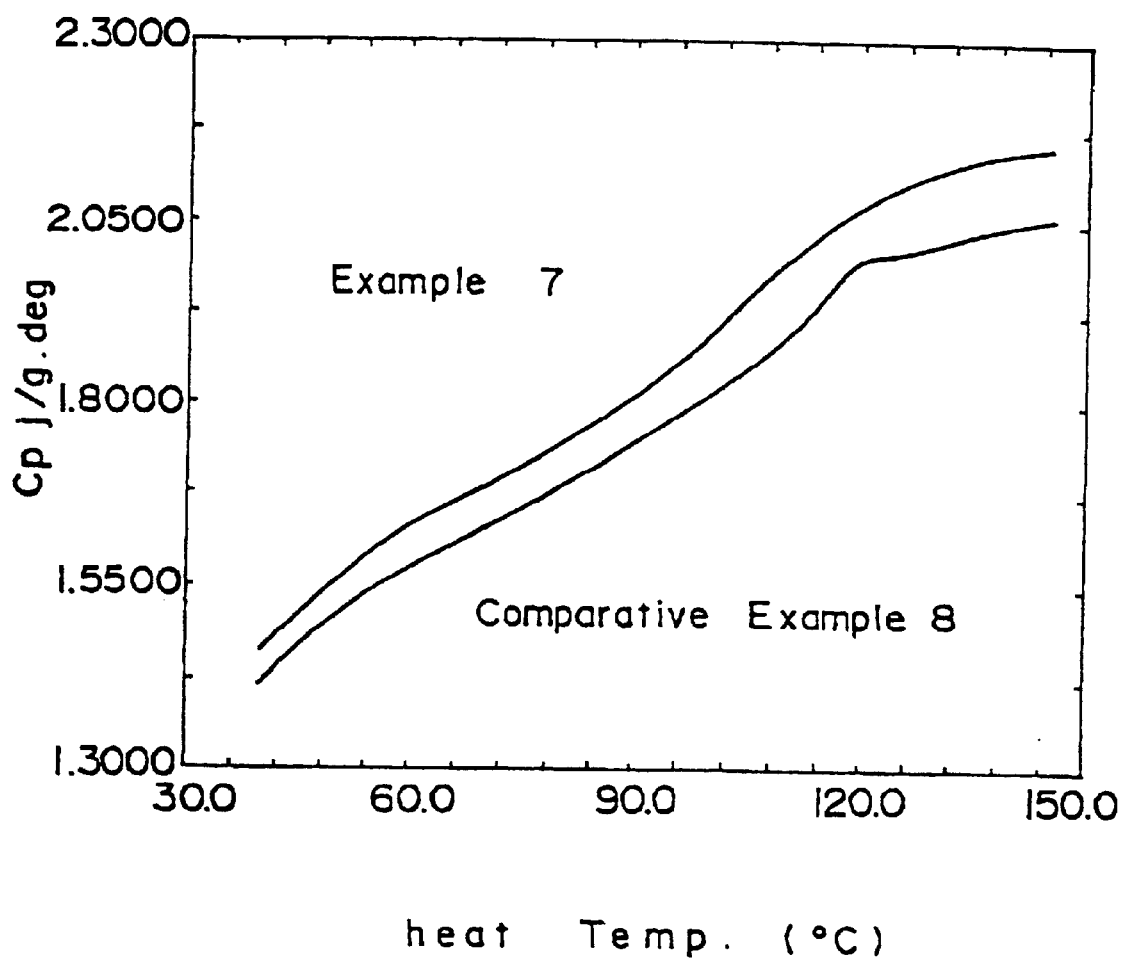
FIG. 4 shows specific heat vs. temperature curve.
Figure 5:
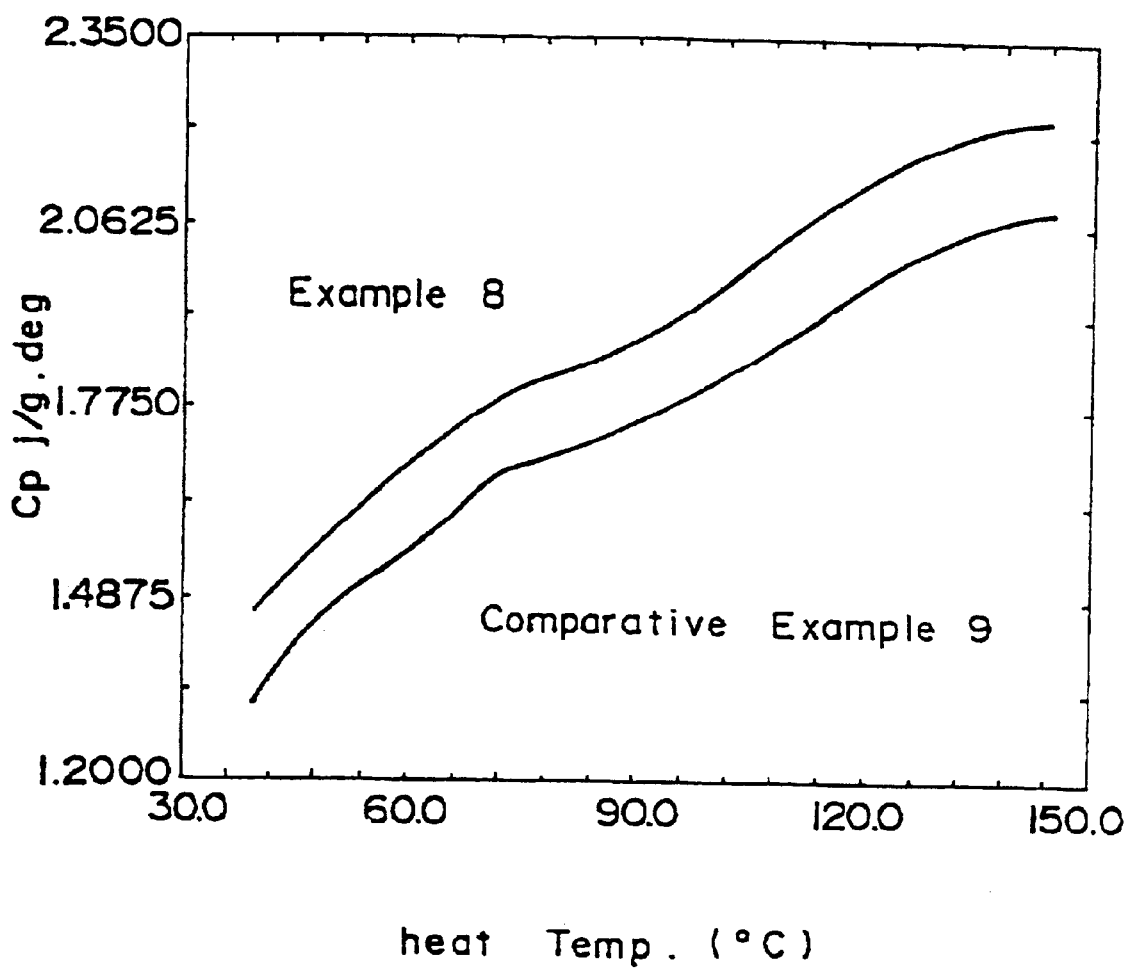
FIG. 5 shows specific heat vs. temperature curve.

It can be understood from Table 6 and FIG. 3 to FIG. 5 that the specific heat capacity of Examples 5 and 7–10 is high compared with each Comparative Example. This fact demonstrates that urethane methacrylate was polymerized homogeneously and compatibly with polymer, resulting in that the interlining of two kinds of polymer chains caused increase of cross-linking density, fineness of phase organization and increase of adhesivity between phases. Thereby, it can be understood that polymers and urethane (metha) acrylate form homogeneous interpenetrating polymer network from the viewpoint of molecular level.

Polymerization Method and Application

EXAMPLE 11–EXAMPLE 28

Curable compositions obtained in Examples 3–10 were mixed with MMA,EG,PG, and TMPT at a ratio shown in Table 7. The resultant mixture was added with 0.6 parts by weight of benzoyl peroxide (BPO) to give monomer comstrength), energy (proportional limit of energy) and fracturing energy. The number of the samples was 5. Measurement was carried out under conditions of distance between fulcrums of 50 mm and cross-head speed of 1 mm/min.

COMPARATIVE EXAMPLE 15 AND COMPARATIVE EXAMPLE 16

Compositions were produced and cured in a manner similar to Examples 11–28, except that Comparative Example 15 used MMA as monomer and PMMA-1 (average molecular weight: 400,000 to 600,000, mean particle size: 40 to 60 micron PMMA) as polymer and that Comparative Example 16 used MMA as monomer and PMMA-1 as polymer.

The evaluation was made in a manner similar to Examples 11–28. The results were summarized in Table 7.

COMPARATIVE EXAMPLE 17

Composition was produced and cured in a manner similar to Examples 11–28, except that MMA and UDMA were used as monomer composition (mixing ratio: 80:20). The evaluation was made in a manner similar to Examples 11–28. The results were summarized in Table 7.

artificial teeth were preserved in water at 50° C. for 7 days. Repeated impact strength, the number of times of impact, and calculation method of score are described below.

TABLE 7

Physical Properties

| | Monomer composition | | | | | Hardness (knoop) | Bending properties | | | Transmittance (%) |
|---|---|---|---|---|---|---|---|---|---|---|
| | MMA | EG | TG | TMPT | Composition | | Strength (MPa) | Energy (g-cm) | Fracturing energy (g-cm) | |
| EX 11 | 70 | 10 | 0 | 0 | EX 3 | 20 | 18.5 | 118.20 | 650.8 | 830.21 | 90.4 |
| EX 12 | 70 | 10 | 0 | 0 | EX 7 | 20 | 1B.9 | 117.83 | 670.4 | 956.23 | 89.5 |
| EX 13 | 80 | 0 | 0 | 0 | EX 3 | 20 | 21.4 | 123.20 | 800.5 | 1109.54 | 88.9 |
| EX 14 | 80 | 0 | 0 | 0 | EX 4 | 20 | 21.3 | 129.94 | 810.4 | 1200 or more | 89.4 |
| EX 15 | 80 | 0 | 0 | 0 | EX 5 | 20 | 20.7 | 132.99 | 758.4 | 949.02 | 90.5 |
| EX 16 | 80 | 0 | 0 | 0 | EX 6 | 20 | 21.3 | 133.01 | 820.1 | 987.13 | 90.2 |
| EX 17 | 80 | 0 | 0 | 0 | EX 7 | 20 | 21.0 | 132.39 | 822.5 | 1200 or more | 89.0 |
| EX 18 | 80 | 0 | 0 | 0 | EX 8 | 20 | 14.8 | 112.25 | 540.4 | 1200 or more | 90.0 |
| EX 19 | 70 | 0 | 10 | 0 | EX 5 | 20 | 19.5 | 124.28 | 706.7 | 1200 or more | 91.0 |
| EX 20 | 70 | 0 | 10 | 0 | EX 7 | 20 | 19.5 | 129.02 | 742.2 | 765.38 | 91.2 |
| EX 21 | 70 | 0 | 0 | 10 | EX 5 | 20 | 19.8 | 125.96 | 748.7 | 1174.47 | 90.2 |
| EX 22 | 70 | 0 | 0 | 10 | EX 7 | 20 | 21.3 | 135.79 | 771.0 | 1200 or more | 87.9 |
| EX 23 | 70 | 10 | 0 | 0 | EX 9 | 20 | 20.5 | 140.67 | 808.2 | 1200 or more | 90.4 |
| EX 24 | 70 | 0 | 10 | 0 | EX 9 | 20 | 20.7 | 128.41 | 680.2 | 1200 or more | 88.3 |
| EX 25 | 70 | 0 | 0 | 10 | EX 10 | 20 | 21.9 | 135.76 | 696.1 | 1200 or more | 90.8 |
| EX 26 | 70 | 10 | 0 | 0 | EX 10 | 20 | 21.8 | 128.71 | 703.7 | 1179.35 | 83.5 |
| EX 27 | 70 | 0 | 10 | 0 | EX 10 | 20 | 21.5 | 125.15 | 572.7 | 620.15 | 84.4 |
| EX 28 | 70 | 0 | 0 | 10 | EX 10 | 20 | 22.5 | 133.31 | 722.7 | 896.66 | 83.5 |
| Comp. EX 15 | 100 | 0 | 0 | 0 | 0 | | 18.0 | 98.0 | 248.5 | 250.45 | 90.5 |
| Comp. EX 15 | 100 | 0 | 0 | 0 | 0 | | 18.0 | 118.54 | 350.5 | 589.28 | 89.3 |
| Comp. EX 17 | 80 | 0 | 0 | 0 | UDMA | 20 | 21.4 | 120.02 | 410.2 | 410.45 | 88.9 |

Evaluation of Artificial Teeth and Resin for Plate

EXAMPLE 29 TO EXAMPLE 46

One hundred parts by weight of a mixture of each monomer composition (liquid) obtained in Examples 11–28 (shown in Table 7) and polymer (powder) of PMMA-2 (mixing ratio (powder:liquid=2:1) were mixed with 0.1 part by weight of pigment by means of a mixer. After swelling, artificial teeth were prepared by use of metal mold for C5 and T5 central insisors to give front teeth made of hard resin. Extra parts of molded teeth was removed. The artificial tooth was bonded to denture base material (PMMA). Denture base adhesion (adhesion strength) and repeated impact strength of the artificial tooth were examined.

Bonding strength of artificial teeth (adhesion strength) to denture base was measured according to item 7.5 bonding test for resin teeth specified in JIS T6506. The results are shown in Table 8.

Repeated impact test on the artificial teeth was made as follows. Artificial teeth was prepared according to item 7.5 bonding test for resin teeth specified in JIS T6506. Incisal enamel section of lingual of the teeth was cut in paralell direction. Stainless steel bar having 1 mm diameter was fallen repeatedly towards the center of the enamel from a position of 10 mm height. Measurement was made after First loading and number of times of impact (100 g×1000).

Second loading and number of times of impact (150 g×1000).

Third loading and number of times of impact (200 g×1000).

The score of impact strength is total values obtained by summing up values calculated by dividing the number of times of impact by 100 in each stage. For example, if artificial tooth is not broken after the tooth was subjected to 1000 times of each maximal impact under 100, 150 and 200 g, the score of 30 points (=1000/100+1000/100+1000/100) is given. The results are shown in Table 8.

TABLE 8

Adhesion Strength between Artificial teeth and Denture Base (PMMA)

| | Adhesion strength (Kgf) | Impact Strength (score) |
|---|---|---|
| EX29 | 22.5 | 25.6 |
| EX30 | 23.5 | 27.6 |

TABLE 8-continued

Adhesion Strength between Artificial teeth
and Denture Base
(PMMA)

|      | Adhesion strength (Kgf) | Impact Strength (score) |
|------|---|---|
| EX31 | 24.5 | 26.9 |
| EX32 | 22.5 | 27.0 |
| EX33 | 21.3 | 28.4 |
| EX34 | 23.6 | 26.0 |
| EX35 | 24.5 | 25.6 |
| EX36 | 24.0 | 28.9 |
| EX37 | 22.5 | 28.0 |
| EX38 | 24.5 | 28.5 |
| EX39 | 24.0 | 27.6 |
| EX40 | 23.6 | 27.5 |

TABLE 8-continued

Adhesion Strength between Artificial teeth
and Denture Base
(PMMA)

|      | Adhesion strength (Kgf) | Impact Strength (score) |
|------|---|---|
| EX41 | 25.5 | 30.0 |
| EX42 | 24.5 | 28.5 |
| EX43 | 25.0 | 30.0 |
| EX44 | 24.5 | 27.5 |
| EX45 | 24.5 | 28.0 |
| EX46 | 25.0 | 29.5 |
| JIS  | 11.0 or more | — |
| Shofu Resin teeth | 15.1 | 21.3 |

EXAMPLES 47 AND 48

A mixture of 92.5 parts by weight of the composition obtained in Example 5 or Example 7 and 7.5 parts by weight of EG was added with 0.6 parts by weight of BPO and mixed homogeneously. The mixture was degassed for 15 to 30 minutes.

COMPARATIVE EXAMPLE 18

A mixture was prepared in a manner similar to Examples 47 and 48, except that a composition of UDMA (92.5 parts by weight) and EG (7.5 parts by weight) was used.

After degassing, the resultant mixture was polymerized in a metal mold under pressure of 100–300 Kgf/cm$^2$ at 80° C. for 5 minutes and cooled for 5 minutes. Polymerization was further carried out for 10 minutes. After polymerization, annealing was carried out at 100° C. for 8 hours. Hardness, bending properties (strength, energy and elasticity modulas) and transmittance were evaluated. The testing method was the same as that in Examples 11–28. The results are shown in Table 9.

Elasticity modulas was given according to three-point bending test.

Transmittance was measured in a manner similar to Examples 3–10.

TABLE 9

Physical Properties of Cured Composition

|  | Composition | | Hardness (Knoop) | Bending properties | | | Transmittance (%) |
|---|---|---|---|---|---|---|---|
|  |  |  |  | Strength (MPa) | Energy (g-cm) | Elasticity modulas (KGF/cm$^2$) |  |
| EX 47 | EX 5 | 92.5 pbw | 21.0 | 103.8 | 890.64 | 168.67 | 86.7 |
|  | EG | 7.5 pbw |  |  |  |  |  |
|  | BPO | 0.6 pbw |  |  |  |  |  |
| EX 48 | EX 7 | 92.5 pbw | 21.8 | 99.48 | 668.89 | 154.16 | 85.8 |
|  | EG | 7.5 pbw |  |  |  |  |  |
|  | BPO | 0.6 pbw |  |  |  |  |  |
| Comp. EX 18 | UDMA | 92.5 pbw | 22.3 | 71.62 | 420.54 | 125.52 | 91.8 |
|  | EG | 7.5 pbw |  |  |  |  |  |
|  | BPO | 0.6 pbw |  |  |  |  |  |

EXAMPLES 49–53

Each composition (1.52 parts by weight) obtained in Examples 5, 7, 8, 9 and 10 was mixed homogeneously with MMA (27.83 parts by weight), 2,2,2-trifluoroethyl acrylate (2.11 parts by weight), EG (2.37 parts by weight), crosslinked polymer of methyl methacrylate with EG (98:2) (43.3 parts by weight), PMMA-2 (21.65 parts by weight) and BPO (0.17 parts by weight). After swelling, samples for bending test, hardness test and transmittance test were prepared (pigment was not added).

EXAMPLES 54–58

Samples were prepared in a manner similar to Examples 49–53, except that PMMA-2 of 43.9 parts by weight was used instead of crosslinked polymer of methyl methacrylate with EG.

COMPARATIVE EXAMPLE 19

Sample was prepared in a manner similar to Example 49, except that UDMA (1.52 parts by weight) was mixed with the composition obtained in Example 5.

After swelling, the samples were polymerized in a metal mold under pressure of 50–300 Kgf/cm$^2$ at 100° C. for 2 minutes and cooled for 5 minutes. Then, polymerization was further carried out under pressure of 50–300 Kgf/cm$^2$ at 120° C. for 10 minutes. After polymerization, annealing was carried out at 100° C. for 8 hours. After the resultant samples were preserved in water at 50° C. for 24 hours, hardness, bending properties (strength, failing energy, elasticity modulas) and transmittance were evaluated. The results are shown in Table 10. Measurement of hardness and bending properties were made in a manner similar to Examples 11–28. The measurement of transmittance was made in a manner similar to Examples 3–10.

TABLE 10

|  | Hardness (Knoop) | Bending Properties | | | Transmittance (%) |
|---|---|---|---|---|---|
|  |  | Strength (MPa) | Energy (g-cm) | Elasticity modulas (Kgf/cm²) |  |
| EX 49 | 16.4 | 116.19 | 372.34 | 292.31 | 90.6 |
| EX 50 | 16.7 | 120.26 | 471.58 | 295.26 | 91.1 |
| EX 51 | 17.0 | 119.43 | 431.13 | 292.89 | 90.4 |
| EX 52 | 17.6 | 124.15 | 354.05 | 301.36 | 88.5 |
| EX 53 | 16.8 | 120.13 | 441.30 | 295.95 | 89.9 |
| EX 54 | 16.6 | 137.86 | 738.04 | 300.43 | 91.2 |
| EX 55 | 17.4 | 127.35 | 731.71 | 289.58 | 90.9 |
| EX 56 | 17.0 | 137.67 | 773.74 | 316.35 | 90.0 |
| EX 57 | 17.2 | 126.86 | 710.57 | 287.77 | 88.7 |
| EX 58 | 17.0 | 125.87 | 708.26 | 279.40 | 90.7 |
| Comp. EX 19 | 16.4 | 104.79 | 283.01 | 285.87 | 88.9 |

It can be clearly understood that all the polymers prepared from the compositions of the present invention showed high bending properties (especially hardness and failing energy) as well as good transmittance in comparison with Comparative Examples.

The polymers of the present invention are remarkably excellent in physical properties (toughness) without crosslinked polymer of methyl methacrylate with EG, and show sufficient transparency.

Evaluation as dental composite resin

EXAMPLES 59 AND 60

The compositions (40 parts by weight) obtained in Examples 5 and 7 were respectively added with 36.5 parts by weight of organic filler, 23.5 parts by weight of quartz filler and 0.6 parts by weight of BPO. The resultant mixture was kneaded to give a dental composite resin.

The composite resins obtained in these Examples were respectively admixed with pigment and subjected to molding process by use of metal mold for anterior tooth and posterior tooth. Adhesion to denture base plate, repeated impact strength, aesthetic properties and physical properties were good.

COMPARATIVE EXAMPLE 20

Dental composite resin was prepared in a manner similar to Examples 59 and 60, except that UDMA was used as binder.

The mixture was polymerized under pressure of 100–300 Kgf/cm² at 120° C. for 10 minutes. After polymerization, the polymerized composition was annealed at 100° C. for 8 hours to give dental composite resin. Hardness, bending properties (strength and failing energy), wear resistance to toothbrush (weared loss:wt %) and transmittance were measured regarding to the obtained dental composite resin. The results are shown in table 11.

Hardness and bending properties were evaluated in a manner similar to Examples 11–28.

The wearing ratio was evaluated by tooth brush wearing test. The testing conditions were as follows:

Toothbrush: Between (trade name) (made by Sunstar K.K.);

Size of test piece: 15 mm long, 20 mm wide and 2.5 mm thick;

The number of test pieces: 4;

Loading: 185 g;

Polishing materials of tooth: tooth paste Green Sunstar (trade name) (made by Sunstar K.K.); and The number of brush: 30,000 times.

The transmittance was measured in a manner similar to Examples 3–10.

TABLE 11

Physical Properties of Dental Composite Resin

|  | Composition |  | Hardness (Knoop) | Bending properties | | Weared loss (wt %) | Transmittance (%) |
|---|---|---|---|---|---|---|---|
|  |  |  |  | Strength (Mpa) | Energy (g-cm) |  |  |
| EX59 | EX5 composition | 40 pbw | 27.3 | 105.81 | 266.19 | 0.59 | 46.9 |
|  | Organic filler | 36.5 pbw |  |  |  |  |  |
|  | Quartz filler | 23.5 pbw |  |  |  |  |  |
|  | PBO | 0.6 pbw |  |  |  |  |  |
| EX60 | EX7 Composition | 40 pbw | 27.0 | 112.79 | 250.37 | 0.60 | 45.5 |
|  | Organic filler | 36.5 pbw |  |  |  |  |  |
|  | Quartz filler | 23.5 pbw |  |  |  |  |  |
|  | PBO | 0.6 pbw |  |  |  |  |  |
| Comp. EX20 | UDMA Composition | 40 pbw | 29.5 | 95.34 | 201.00 | 0.48 | 46.4 |
|  | Organic filler | 36.5 pbw |  |  |  |  |  |
|  | Quartz filler | 23.5 pbw |  |  |  |  |  |
|  | BPO | 0.6 pbw |  |  |  |  |  |

Adhesion Test of Dentin

EXAMPLES 61 AND 62

The composition obtained in Example 4 or Example 7 (60 parts by weight), 40 parts by weight of EG, 3 parts by weight of 4-acryloxyethyltrimellitic acid (referred to as "4-AET" hereinafter), 1.4 parts by weight of dimethylaminoethyl methacrylate (referred to as "MADMAE" hereinafter), 0.7 parts by weight of camphorquinone and 3 parts by weight of 2-HEMA were mixed to give an adhesive for dentin.

Adhesion test of dentin to composite was carried out as follows. The tongue side of fresh front tooth enamel of cow was polished by #600 Emery paper. After polishing, the tooth was etched with phosphoric acid for 15 seconds, washed with water and air-dried. Area for adhesion had 4 mm diameter. The adhesive was applied to the area through spacer having 40 μm thickness and photopolymerized by irradiation of visible light for 30 seconds. After polymerization, the polymerized area was polished by #600 ??Emery Paper. A stainless steel bar was adhered to the polished area with LITE FIL (made by Shofu K.K.). The obtained sample was preserved in water at 37° C. for 24 hours. Then, tensile adhesion strength was evaluated by means of universal testing machine (Autograph AG5000B) (made by Shimazu Seisakusyo K.K.) under conditions of crosshead speed of 1 mm/min. The results are shown in Table 12.

Comparative Example was carried out in a manner similar to the above except that carboxylate cement and resin adhesive avairable in the market were used as an adhesive. The results are also shown in Table 12.

TABLE 12

Adhesion Test of Dentine

|  |  |  | Adhesion Properties | |  |
|---|---|---|---|---|---|
|  | Composition |  | Strength (Mpa) | Peel energy (g-cm) | Maximal strength (Mpa) |
| EX61 | EX4 composition | 60 pbw | 22.05 (6.20) | 37.47 (15.90) | 29.08 |
|  | EG | 40 pbw |  |  |  |
|  | 4-AET | 3 pbw |  |  |  |
|  | 2HEMA | 3 pbw |  |  |  |
|  | MADMAE | 1.4 pbw |  |  |  |
|  | Camphor-quinone | 0.7 pbw |  |  |  |
| EX62 | EX7 composition | 60 pbw | 25.03 (1.96) | 45.81 (6.88) | 27.32 |
|  | EG | 40 pbw |  |  |  |
|  | 4-AET | 3 pbw |  |  |  |
|  | 2HEMA | 3 pbw |  |  |  |
|  | MADMAE | 1.4 pbw |  |  |  |
|  | Camphoe-quinone | 0.7 pbw |  |  |  |
| Comp. EX | Carboxylate cement |  | 4.0~6.0 18~20.0 | 23.0~30.0 |  |
|  | Resin adhesive available in the market |  |  |  |  |

Value inside ( ) means standard deviation

Adhesion strength to PMMA and PC of denture base materials

EXAMPLES 63, 64, 65, 66, 67, 68, 70 AND 71

One part by weight of each composition obtained in Examples 4, 5, 6, 7, 9, and 10 was mixed with 99 parts by weight of methylene chloride to give an adhesive for rebasing material.

Surface of flat board made of denture base material (trade name; SHOFU URBAN) (made by Shofu K.K.) or reinforced polycarbonate (made by Teijin K.K.) was polished by #1000 Emery Paper and buffed. The surface to be adhered had 5 mm diameter. The adhesive was applied to the surface and methylene chloride solvent was vaporized. Stainless steel member (12 mm diameter, 11 mm height and 9 mm inner diameter) having a hole of 5 mm across was fixed on the surface. A mixture of liquid material with powder of resin for dental plate rebasing (Tokuso Rebase) (made by Tokuyama K.K.) prepared according to the usual method was poured through the hole of the stainless steel.

The poured material was left to stand for 15–20 minutes to cure Tokuso Rebase. Then the stainless steel member was taken away. Then, tenisle adhesion strength was evaluated by means of Autograph AG5000B under conditions of crosshead speed of 1 mm/min. The results are shown in Table 12. With respect to Examples 63–67, the measurement was made after the sample was preserved in water at 50° C. for 7 days. With respect to Examples 68–71, the measurement was made after the sample was subjected to thermal cycles of 30,000 times at 5° C. and 60° C. The results are shown in Table 13.

COMPARATIVE EXAMPLE 21

UDMA (1 part by weight) and 99 parts by weight of methylene chloride were mixed to give an adhesive for rebasing material. The adhesive was handled and evaluated in a manner similar to Example 63. The results are shown in Table 13.

COMPARATIVE EXAMPLE 22

PEMA (0.02 parts by weight), 0.98 parts by weight of UDMA and 99 parts by weight of methylene chloride were mixed to give an adhesive for rebasing matarial. The adhesive was handled in a manner similar to Example 63. The results are shown in Table 13.

COMPARATIVE EXAMPLE 23

An adhesive for rebasing (Rebase Aid) (made by Tokuyama K.K.) was used according to the indication of the maker. The adhesive was handled and evaluated in a manner similar to Example 63. The results are shown in Table 13.

COMPARATIVE EXAMPLE 24

Rebase Aid was used according to the indication of the maker. The adhesive was handled and evaluated in a manner similar to Example 68.

TABLE 13

| Composition | | | Adhesion Properties | |
|---|---|---|---|---|
| Example Methylene cloride | 1 pbw 99 pbw | Surface to be bonded | Strength (MPa) | Peel energy (g-cm) |
| EX63 | EX4 | PMMA | 11.5 | 7.80 |
| EX64 | EX6 | PMMA | 12.0 | 7.75 |
| EX65 | EX7 | PMMA | 12.5 | 8.57 |
| EX66 | EX9 | PMMA | 14.5 | 14.95 |
| EX67 | EX10 | PMMA | 18.5 | 20.92 |
| EX68 | EX5 | PC | 6.65 | 17.28 |
| EX69 | EX7 | PC | 6.31 | 18.33 |
| EX70 | EX9 | PC | 7.21 | 19.00 |
| EX71 | EX10 | PC | 6.17 | 14.03 |
| Comp. EX 21 | UDMA | PMMA | 0.50 | 0.0 |
| Comp. EX 22 | UDMA/PEMA | PMMA | 2.15 | 1.21 |
| Comp. EX 23 | Toxso | PMMA | 3.73 | 1.25 |
| Comp. EX 24 | Toxso | PC | 7.52 | 14.85 |

EXAMPLE 72

The composition obtained in Example 7 (70 parts by weight) was mixed with 30 parts by weight of styrol. The resultant composition had specific gravity of 1.15–1.16, viscosity of 2,000 (20° C., CPS). The obtained composition (100 parts by weight) was added with 1 part by weight of BPO and dimethylaniline of 0.3 parts by weight. The mixture was cured at room temperature and heated at 120° C. for 5 hours to give a test sample. Mechanical strength etc. of the sample was measured. The results are shown in Table 14.

EXAMPLE 73

Laminated plate was prepared by use of non-treated non-alkali twill weave glass fiber (EC-181BHVAX; made by Nittobo K.K.) under the same molding and composition conditions as in Example 72. The results are shown in Table 14.

COMPARATIVE EXAMPLES 25 and 26

Unsaturated polyester resin (??RipoxyR-800)(made by Showa Kobunshi K.K.) was molded in a manner similar to Example 72 and Example 73. Thus, Comparative Example 25 and Comparative Example 26 were given. The results are shown in Table 14.

TABLE 14

|  | EX72 | EX73 | Comp. EX25 | Comp. EX26 |
| --- | --- | --- | --- | --- |
| Content of resin (%) | 100 | 47 | 100 | 47 |
| Specific gravity | 1.26 | 1.89 | 1.18 | 1.9 |
| Rockwell hardness | M100 | M99 | M-115 | M-110 |
| Tensile strength (kgf/mm$^2$) | 5.4 | 56.0 | 3.6 | 26.5 |
| Compressive strength (kgf/mm$^2$) | 20.1 | 60.3 | 27.3 | 50.6 |
| Bending strength (kgf/mm$^2$) | 15.0 | 40.5 | 11.4 | 30.5 |
| Bending modulas (kgf/mm$^2$) | 630 | 3906 | 335 | 1640 |
| Charpy impact (kgf/mm$^2$) | 5.2 | 132 | 3.1 | 84.7 |
| Water absorption (%) | 1.2 | — | 1.57 | — |

EXAMPLE 74

This example shows repairing of a concrete structure. First, 50 parts by weight of the composition obtained in Example 7 was mixed with 50 parts by weight of styrol and an adequate amount of BPO and dimethylaniline to give a composition for injection. V-cuts were made in crevice portions of the concrete. Diameter and length of injection pipe was adjusted adequately depending on width of the V-cuts. Fifty parts by weight of the composition obtained above was added with 50 parts by weight of dried sand having 80–150 mesh to give a putty-like composition. The V-cuts were sealed by the putty-like composition, except for the portions where injection pipes were installed. Then, the composition for injection was poured through one of the pipes. When overflowing the pipe, the composition for injection was poured through a next one of the pipes. This process was repeated. After the composition for injection was cured, the injection pipes were removed. The excessively supplied composition was scraped. Insufficiently supplied portions were added with the putty-like composition. Thus, the treatment of surface was finished. BPO is usually added to the above composition at an amount of about 0.5–2 parts by weight, and dimethylaniline at an amount of about 0.5–1 parts by weight, on the basis of 100 parts by weight of the above composition. But, it is necessary that each amount thereof is adjusted depending on temperature (temperature of a concrete), width and depth of crevice, and injection pressure etc.

EXAMPLE 75

The composition obtained in Example 7 (50 parts by weight), 50 parts by weight of styrol, 1 part by weight of BPO, 0.5 parts by weight of dimethylaniine were mixed. The mixture was further added with 450 parts by weight of No. 3 siliceous sand, 450 parts by weight of No. 6 siliceous sand and 50 parts by weight of a mixture (1:1 weight ratio) of pigment (titanium oxide in the case of white color, carbon black in the case of black color, and a mixture of titanium oxide with bisazo-series organic pigment in the case of yellow color; any other adequate mixture of inorganic pigment or organic pigment) with silica super fine particles. Paved surface was cleaned, dried and coated with tackcoat (0.3 Kgf/cm$^2$). The resultant mixture was applied onto the paved surface.

The composition of the present invention can be applied to pavement of traffic divisions of main road, general side walk, pedestrian overpass and parking lot, tennis court, and floor materials of factory. The composition of the present invention may be also applied to construction method in which calcined bauxite, or emery, nickel slag etc. is sprayed on the above resin as nonslip pavement.

EXAMPLE 76

The composition of Example 61 (80 parts by weight), 0.1 part by weight of wax, 20 parts by weight of thinner were mixed to give clear lacquer. The lacquer was applied to wood and steel plate and dried. Test was carried out according to the description of acrylic resin varnish in JISK5653. The results satisfied all quality standards in each item. This lacquer could be dried within 10 minutes under direct rays of the sun in summer because the lacquer can be cured by visible lights.

In the curable composition of the present invention, polymer and monomer which is neither soluble nor swellable in the polymer are mixed homogeneously from the viewpoint of molecular level. Therefor, the curable composition of the present invention is useful in many ways as above described. The cured composition thereof has utility values and physical properties which can not be achieved by conventional heterogeneous mixture of polymer and non-swellable monomer.

The cured composition of the present invention is excellent in bending properties, transparency and adhesion, and suitable for resin moldings and dental materials required of mechanical strength (durability) and transparency.

What is claimed is:

1. A curable composition, in which a polymer and urethane (meth)acrylate which is essentially neither soluble nor swellable in the polymer are mixed homogeneously, wherein the curable composition is obtained by reacting an isocyanate compound with a (meth)acrylate compound having hydroxyl group in a homogeneous solution containing the polymer.

2. The composition of claim 1, in which the polymer is contained at an amount of 5.2 to 47 g per 1 mole of isocyanate compound used for synthesis of the urethane (metha)acrylate.

3. The composition of claim 2, in which a mean molecular weight of the polymer is within the range between 100,000 and 1,000,000.

4. The composition of claim 2, in which the polymer is selected from the group consisting of thermoplastic resins.

5. The composition of claim 2, in which urethane (metha)acrylate has at least one of acryloyl groups, and an urethane group per one molecule.

6. The composition of claim 1, in which a mean molecular weight of the polymer is within the range between 100,000 and 1,000,000.

7. The composition of claim 6, in which the polymer is selected from the group consisting of thermoplastic resins.

8. The composition of claim 6, in which urethane (metha)acrylate has at least one of acryloyl groups, and an urethane group per one molecule.

9. The composition of claim 1, in which the polymer is selected from the group consisting of thermoplastic resins.

10. The composition of claim 9, in which urethane (metha)acrylate has at least one of acryloyl groups, and an urethane group per one molecule.

11. The composition of claim 1, in which the urethane (metha)acrylate has at least one of acryloyl groups, and an urethane group per one molecule.

12. The composition of claim 1, produced by reacting an isocyanate compound in a homogeneous solution containing the polymer and a (metha)acrylate having a hydroxyl group.

13. The composition of claim 1, produced by reacting a (metha)acrylate having a hydroxyl group in a homogeneous solution containing the polymer and an isocyanate compound.

14. The composition of claim 1, produced by reacting a polyalcohol in a homogeneous solution containing the polymer with an excessive isocyanate compound, and then further reacting the isocyanate compound with a (metha)acrylate compound having a hydroxyl group.

15. A dental curable composition, comprising the curable composition of claim 1.

16. The dental curable composition of claim 15, which is used for restorative dental materials, dental fillers and dental denture base materials.

17. A curable composition of claim 1, which is used for adhesives, molding materials and coating compounds.

18. A dental cured composition, produced by curing the curable composition of claim 1.

19. A cured composition of claim 18, which is used for artificial teeth materials or crown restoration materials.

* * * * *